(12) United States Patent
Marusich et al.

(10) Patent No.: US 12,329,445 B2
(45) Date of Patent: Jun. 17, 2025

(54) RF ABLATION SYSTEMS AND METHODS USING AN INTEGRATED CANNULA AND ELECTRODE

(71) Applicant: Boston Scientific Neuromodulation Corporation, Valencia, CA (US)

(72) Inventors: Kathryn Rose Marusich, Eden Prairie, MN (US); Kevin Peng Wang, Fremont, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 736 days.

(21) Appl. No.: 17/553,555

(22) Filed: Dec. 16, 2021

(65) Prior Publication Data

US 2022/0202485 A1 Jun. 30, 2022

Related U.S. Application Data

(60) Provisional application No. 63/131,260, filed on Dec. 28, 2020.

(51) Int. Cl.
  *A61B 18/14* (2006.01)
  *A61B 18/00* (2006.01)
  *A61B 18/12* (2006.01)

(52) U.S. Cl.
  CPC ...... *A61B 18/1492* (2013.01); *A61B 18/1206* (2013.01); *A61B 2018/00083* (2013.01);
  (Continued)

(58) Field of Classification Search
  CPC ............ A61B 18/1492; A61B 18/1206; A61B 2018/00083; A61B 2018/00172;
  (Continued)

(56) References Cited

U.S. PATENT DOCUMENTS

| 4,411,266 A | 10/1983 | Cosman |
| 4,565,200 A | 1/1986 | Cosman |

(Continued)

FOREIGN PATENT DOCUMENTS

| WO | 99/40859 | 8/1999 |
| WO | 99/40860 | 8/1999 |

(Continued)

OTHER PUBLICATIONS

U.S. Appl. No. 63/138,092, filed Jan. 15, 2021.

(Continued)

*Primary Examiner* — Linda C Dvorak
*Assistant Examiner* — Abigail Bock
(74) *Attorney, Agent, or Firm* — Branch Partners PLLC; Bruce E. Black

(57) ABSTRACT

An integrated cannula/RF electrode for an RF ablation system includes a cannula including a cannula hub and a shaft extending from the cannula hub, wherein the shaft includes a distal portion; an RF electrode including a distal portion, wherein at least a portion of the RF electrode is permanently disposed within the cannula; and a deployment mechanism coupled to the RF electrode and either coupled to the cannula hub or extending from the cannula hub, wherein the deployment mechanism includes an actuator coupled to the RF electrode and is configured to extend the distal portion of the RF electrode out of the distal portion of the shaft of the cannula by actuation of the actuator.

17 Claims, 4 Drawing Sheets

(52) U.S. Cl.
CPC ........... *A61B 2018/00172* (2013.01); *A61B 2018/00577* (2013.01); *A61B 2018/00946* (2013.01); *A61B 2018/00952* (2013.01); *A61B 2218/002* (2013.01)

(58) Field of Classification Search
CPC ........... A61B 2018/00577; A61B 2018/00946; A61B 2018/00952; A61B 2218/002
See application file for complete search history.

(56) References Cited

U.S. PATENT DOCUMENTS

| | | | |
|---|---|---|---|
| 4,566,454 A | 1/1986 | Mehl et al. | |
| 4,597,379 A | 7/1986 | Kihn et al. | |
| 4,727,874 A | 3/1988 | Bowers et al. | |
| 4,807,620 A | 2/1989 | Strul et al. | |
| 5,360,009 A | 11/1994 | Herskovitz | |
| 5,433,739 A | 7/1995 | Sluijter et al. | |
| 5,571,147 A | 11/1996 | Sluijter et al. | |
| 5,728,143 A | 3/1998 | Gough et al. | |
| 5,769,847 A | 6/1998 | Panescu et al. | |
| 5,951,546 A | 9/1999 | Lorentzen | |
| 5,983,141 A | 11/1999 | Sluijter et al. | |
| 6,070,845 A | 6/2000 | Herskovitz | |
| 6,104,959 A | 8/2000 | Spertell | |
| 6,161,048 A | 12/2000 | Sluijter et al. | |
| 6,203,524 B1 | 3/2001 | Burney et al. | |
| 6,245,065 B1 | 6/2001 | Panescu et al. | |
| 6,246,912 B1 | 6/2001 | Sluijter et al. | |
| 6,259,952 B1 | 7/2001 | Sluijter et al. | |
| 6,301,506 B1 | 10/2001 | Den Boer et al. | |
| 6,321,120 B1 | 11/2001 | Surbeck et al. | |
| 6,341,429 B1 | 1/2002 | Herskovitz | |
| 6,397,106 B1 | 5/2002 | DeBrouse | |
| 6,402,739 B1 | 6/2002 | Neev | |
| 6,428,537 B1 | 8/2002 | Swanson et al. | |
| 6,440,127 B2 | 8/2002 | McGovern et al. | |
| 6,447,505 B2 | 9/2002 | McGovern et al. | |
| 6,482,204 B1 | 11/2002 | Lax et al. | |
| 6,517,534 B1 | 2/2003 | McGovern et al. | |
| 6,530,922 B2 | 3/2003 | Cosman et al. | |
| 6,692,493 B2 | 2/2004 | McGovern et al. | |
| 6,743,226 B2 | 6/2004 | Cosman et al. | |
| 6,843,789 B2 | 1/2005 | Goble | |
| 6,853,864 B2 | 2/2005 | Litovitz | |
| 6,869,430 B2 | 3/2005 | Balbierz et al. | |
| 7,363,071 B2 | 4/2008 | Damasco et al. | |
| 7,522,953 B2 | 4/2009 | Kaula et al. | |
| 7,553,309 B2 | 6/2009 | Buysse et al. | |
| 7,574,257 B2 | 8/2009 | Rittman, III | |
| 7,725,155 B2 | 5/2010 | Dowlatshahi | |
| 7,749,218 B2 | 7/2010 | Pellegrino et al. | |
| 7,799,024 B2 | 9/2010 | Randall | |
| 8,123,782 B2 | 2/2012 | Altarac et al. | |
| 8,128,662 B2 | 3/2012 | Altarac et al. | |
| 8,273,108 B2 | 9/2012 | Altarac et al. | |
| 8,277,488 B2 | 10/2012 | Altarac et al. | |
| 8,292,922 B2 | 10/2012 | Altarac et al. | |
| 8,361,607 B2 | 1/2013 | Higuchi et al. | |
| 8,425,559 B2 | 4/2013 | Altarac et al. | |
| 8,512,333 B2 | 8/2013 | Epstein et al. | |
| 8,518,037 B2 | 8/2013 | Young | |
| 8,613,747 B2 | 12/2013 | Altarac et al. | |
| 8,808,284 B2 | 8/2014 | Pellegrino et al. | |
| 8,864,828 B2 | 10/2014 | Altarac et al. | |
| 8,945,183 B2 | 2/2015 | Altarac et al. | |
| 8,979,830 B2 | 3/2015 | Hennings | |
| 8,992,522 B2 | 3/2015 | Pellegrino et al. | |
| 9,039,701 B2 | 5/2015 | Pellegrino et al. | |
| 9,119,680 B2 | 9/2015 | Altarac et al. | |
| 9,155,570 B2 | 10/2015 | Altarac et al. | |
| 9,155,572 B2 | 10/2015 | Altarac et al. | |
| 9,161,783 B2 | 10/2015 | Altarac et al. | |
| 9,173,676 B2 | 11/2015 | Pellegrino et al. | |
| 9,186,186 B2 | 11/2015 | Reglos et al. | |
| 9,393,055 B2 | 7/2016 | Altarac et al. | |
| 9,532,812 B2 | 1/2017 | Altarac et al. | |
| 9,572,603 B2 | 2/2017 | Altarac et al. | |
| 9,717,552 B2 | 8/2017 | Cosman et al. | |
| 9,861,398 B2 | 1/2018 | Altarac et al. | |
| 9,956,011 B2 | 5/2018 | Altarac et al. | |
| 9,956,032 B1 | 5/2018 | Cosman et al. | |
| 10,080,587 B2 | 9/2018 | Altarac et al. | |
| 10,111,703 B2 | 10/2018 | Cosman, Jr. et al. | |
| 10,136,937 B1 | 11/2018 | Cosman, Jr. et al. | |
| 10,136,942 B1* | 11/2018 | Cosman, Jr ........ | A61B 18/1477 |
| 10,136,943 B1 | 11/2018 | Cosman, Jr. et al. | |
| 10,166,047 B2 | 1/2019 | Altarac et al. | |
| 10,194,971 B2 | 2/2019 | Wegrzyn, III et al. | |
| 10,342,606 B2 | 7/2019 | Cosman et al. | |
| 10,357,258 B2 | 7/2019 | Patel et al. | |
| 10,363,063 B2 | 7/2019 | Cosman | |
| 10,420,591 B2 | 9/2019 | Snell et al. | |
| 10,463,423 B2 | 11/2019 | Sutton et al. | |
| 10,478,246 B2 | 11/2019 | Pellegrino et al. | |
| 10,517,611 B2 | 12/2019 | Patel et al. | |
| 10,548,654 B2 | 2/2020 | Curley | |
| 10,588,687 B2 | 3/2020 | Cosman, Jr. et al. | |
| 10,610,267 B2 | 4/2020 | Altarac et al. | |
| 10,631,915 B1 | 4/2020 | Cosman | |
| 10,639,098 B2 | 5/2020 | Cosman et al. | |
| 10,639,101 B2 | 5/2020 | Cosman et al. | |
| 10,653,456 B2 | 5/2020 | Altarac et al. | |
| 10,709,502 B2 | 7/2020 | Viswanathan | |
| 10,835,295 B2 | 11/2020 | Altarac et al. | |
| 10,835,297 B2 | 11/2020 | Altarac et al. | |
| 11,013,539 B2 | 5/2021 | Altarac et al. | |
| 11,076,893 B2 | 8/2021 | Altarac et al. | |
| 11,207,100 B2 | 12/2021 | Donovan et al. | |
| 11,229,461 B2 | 1/2022 | Altarac et al. | |
| 2002/0077683 A1 | 6/2002 | Westlund et al. | |
| 2002/0156472 A1 | 10/2002 | Lee et al. | |
| 2002/0165531 A1 | 11/2002 | Goble | |
| 2003/0032951 A1 | 2/2003 | Rittman et al. | |
| 2003/0212390 A1 | 11/2003 | Chen et al. | |
| 2005/0065509 A1 | 3/2005 | Coldwell et al. | |
| 2005/0277918 A1 | 12/2005 | Shah et al. | |
| 2007/0032835 A1 | 2/2007 | Rittman | |
| 2008/0195152 A1 | 8/2008 | Altarac et al. | |
| 2008/0200972 A1 | 8/2008 | Rittman et al. | |
| 2008/0262490 A1 | 10/2008 | Williams | |
| 2009/0138046 A1 | 5/2009 | Altarac et al. | |
| 2009/0254019 A1* | 10/2009 | Gehl ................. | A61B 18/1477 604/21 |
| 2010/0114093 A1 | 5/2010 | Mahapatra et al. | |
| 2010/0222747 A1 | 9/2010 | Wenchell et al. | |
| 2010/0249750 A1 | 9/2010 | Racz et al. | |
| 2011/0028836 A1* | 2/2011 | Ranpura ............ | A61B 90/39 600/432 |
| 2011/0288540 A1 | 11/2011 | Wright et al. | |
| 2012/0203064 A1 | 8/2012 | Wynberg | |
| 2013/0345699 A1 | 12/2013 | Brannan et al. | |
| 2014/0066917 A1 | 3/2014 | Cosman, Jr. et al. | |
| 2014/0081260 A1 | 3/2014 | Cosman, Jr. et al. | |
| 2014/0121658 A1 | 5/2014 | Cosman, Jr. et al. | |
| 2014/0276800 A1 | 9/2014 | Batchelor et al. | |
| 2015/0182234 A1 | 7/2015 | Mahoney et al. | |
| 2015/0305799 A1 | 10/2015 | Trieu | |
| 2016/0206362 A1 | 7/2016 | Mehta et al. | |
| 2016/0242822 A1 | 8/2016 | Altarac et al. | |
| 2016/0278791 A1 | 9/2016 | Pellegrino et al. | |
| 2017/0004951 A1 | 1/2017 | Weisz et al. | |
| 2017/0049514 A1 | 2/2017 | Cosman | |
| 2017/0325832 A1* | 11/2017 | Jadhav ............... | F16H 19/02 |
| 2018/0221084 A1* | 8/2018 | Jayaraman ........... | A61M 1/774 |
| 2018/0318061 A1 | 11/2018 | Clarke et al. | |
| 2019/0110833 A1 | 4/2019 | Pellegrino et al. | |
| 2019/0201057 A1 | 7/2019 | Altarac et al. | |
| 2019/0223948 A1 | 7/2019 | Stewart et al. | |
| 2020/0038091 A1 | 2/2020 | Cao et al. | |
| 2020/0038096 A1 | 2/2020 | Schepis et al. | |
| 2020/0139144 A1 | 5/2020 | Cosman et al. | |
| 2020/0146744 A1 | 5/2020 | Defosset et al. | |
| 2020/0281646 A1 | 9/2020 | Pellegrino et al. | |

(56) References Cited

U.S. PATENT DOCUMENTS

| | | | |
|---|---|---|---|
| 2020/0330153 | A1 | 10/2020 | Cosman, Jr. et al. |
| 2020/0383707 | A1 | 12/2020 | Kidman et al. |
| 2021/0038298 | A1 | 2/2021 | Scott et al. |
| 2021/0100592 | A1 | 4/2021 | Seifert et al. |
| 2021/0121224 | A1 | 4/2021 | Ranpura et al. |
| 2021/0236191 | A1 | 8/2021 | Wang et al. |
| 2021/0322063 | A1 | 10/2021 | Altarac et al. |
| 2021/0369394 | A1 | 12/2021 | Braido et al. |
| 2021/0393315 | A1 | 12/2021 | McGregor et al. |
| 2022/0061894 | A1 | 3/2022 | Altarac et al. |
| 2022/0202484 | A1 | 6/2022 | Wang |
| 2022/0226039 | A1 | 7/2022 | Wang |
| 2022/0323147 | A1 | 10/2022 | Hata et al. |
| 2022/0401085 | A1* | 12/2022 | Cosman, Jr. ....... A61B 18/1477 |
| 2024/0108361 | A1 | 4/2024 | Johnson et al. |
| 2024/0108394 | A1 | 4/2024 | Bates et al. |
| 2024/0245445 | A1 | 7/2024 | Bates |
| 2024/0245449 | A1 | 7/2024 | Bates |
| 2024/0277384 | A1 | 8/2024 | Malinowski |

FOREIGN PATENT DOCUMENTS

| | | |
|---|---|---|
| WO | 00/59394 | 10/2000 |
| WO | 2007121143 | 10/2007 |
| WO | 2014130031 | 8/2014 |
| WO | WO2022011115 | 1/2022 |

OTHER PUBLICATIONS

Cosman et al. "Theoretical Aspects of Radiofrequency Lesions in the Dorsal Root Entry Zone," Neurosurgery, vol. 15, No. 6, p. 945-950 (1984).
U.S. Appl. No. 18/373,586, filed Sep. 27, 2023.
U.S. Appl. No. 18/373,626, filed Sep. 27, 2023.
Rhame EE, Levey KA, Gharibo CG. Successful treatment of refractory pudendal neuralgia with pulsed radiofrequency. Pain Physician. May-Jun. 2009;12(3):633-8. PMID: 19461829.
Todorov L. Pulsed radiofrequency of the sural nerve for the treatment of chronic ankle pain. Pain Physician. May-Jun. 2011;14(3):301-4. PMID: 21587334.
Hemostasis Vales—Qosina—URL: hllps://www.qosina.com/vascular-access-hemostasis-valves 9 pages—retrieved Nov. 13, 2019.
"Coolief* Cooled Radio Frequency Kit—Instructions for Use" Halyard—dated Feb. 9, 2017—8 pages.
Cobra R-F™—Epimed—URL: https://www.epimed.com/products/cobra-r-f/—retrieved Jan. 27, 2021.
Hyso et al., "Epimed Launches "Cobra" R-F™ Dual Use Radiofrequency Cannula" Cision—PR Web—Jan. 17, 2019 3 pages.
"Venom cannula and electrode system"—Stryker—retrieved Sep. 8, 2020 URL: https://www.stryker.com/us/en/Interventional-spine/products/venom-cannula-and-electrode-system.html.
"RF Trident™ Cannulae" Diros Technology Inc. Nov. 11, 2017 URL: https://web.archive.org/web/20171117054945/https://dirostech.com/product-details/rf-tridenttrident-hybrid-cannulae/.
Cedeno et al., "Comparisons of Lesion Volumes and Shapes Produced by a Radiofrequency System with a Cooled, a Protruding, or a Monopolar Probe" Pain Physician 2017; 20:E915-E922 • ISSN 2150-1149.
Correspondence from Department of Health and Human Services to George Darmos at Diros Technology, Inc.—dated Jul. 30, 2015—11 pages.
Correspondence from Department of Health and Human Services to Christina McKee—dated Mar. 28, 2013; 7 pages.
U.S. Appl. No. 63/130,519, filed Dec. 24, 2020.

* cited by examiner

RF ABLATION SYSTEMS AND METHODS USING AN INTEGRATED CANNULA AND ELECTRODE

CROSS-REFERENCE TO RELATED APPLICATIONS

This application claims the benefit under 35 U.S.C. § 119(e) of U.S. Provisional Patent Application Ser. No. 63/131,260, filed Dec. 28, 2020, which is incorporated herein by reference.

FIELD

The present disclosure is directed to the area of radiofrequency (RF) ablation systems and methods of making and using the systems. The present disclosure is also directed to RF ablation systems and methods that include an integrated cannula and electrode, as well as methods of making and using the same.

BACKGROUND

Radiofrequency (RF) generators and electrodes can be used for pain relief or functional modification. Radiofrequency ablation (RFA) is a safe, proven means of interrupting pain signals, such as those coming from irritated facet joints in the spine, genicular nerves in the knee, and femoral and obturator nerves in the hip. Radiofrequency current is used to heat up a small volume of nerve tissue, thereby interrupting pain signals from that specific area. Radiofrequency ablation is designed to provide long-lasting pain relief.

For example, an RF electrode can be positioned near target tissue and then used to heat the target tissue by RF power dissipation of the RF signal output in the target tissue. Temperature monitoring of the target tissue by a temperature sensor in the electrode may be used to control the process.

BRIEF SUMMARY

One aspect is an integrated cannula/RF electrode for an RF ablation system that includes a cannula including a cannula hub and a shaft extending from the cannula hub, wherein the shaft includes a distal portion; an RF electrode including a distal portion, wherein at least a portion of the RF electrode is permanently disposed within the cannula; and a deployment mechanism coupled to the RF electrode and either coupled to the cannula hub or extending from the cannula hub, wherein the deployment mechanism includes an actuator coupled to the RF electrode and is configured to extend the distal portion of the RF electrode out of the distal portion of the shaft of the cannula by actuation of the actuator.

In at least some aspects, the deployment mechanism is further configured to retract the distal portion of the RF electrode back into the cannula.

In at least some aspects, the deployment mechanism is a slider deployment mechanism and the actuator is a slider. In at least some aspects, the slider deployment mechanism further includes a case that defines a track for the slider. In at least some aspects, the slider deployment mechanism further includes a rod coupled to the slider and to the RF electrode.

In at least some aspects, the deployment mechanism is a rotational deployment mechanism and the actuator is a rotatable actuator. In at least some aspects, the rotational deployment mechanism further includes a screw coupled to the rotatable actuator and the RF electrode. In at least some aspects, the screw is hollow.

In at least some aspects, the integrated cannula/RF electrode further includes a cable extending from the cannula hub and electrically coupled to the RF electrode. In at least some aspects, the integrated cannula/RF electrode further includes a fluid injection port for injecting fluid through the cannula hub and the cannula. In at least some aspects, the integrated cannula/RF electrode further includes a fluid tube coupled to the cannula hub and the fluid injection port. In at least some aspects, a portion of the interior of the shaft is electrically insulated.

Another aspect is an RF ablation system that includes any of the integrated cannula/RF electrodes described above and an RF generator coupleable or coupled to the integrated cannula/RF electrode. In at least some aspects, the RF ablation system further includes an extension configured to couple the integrated cannula/RF electrode to the RF generator.

Yet another aspect is a method of using any of the integrated cannula/RF electrodes described above. The method includes operating the actuator of the deployment mechanism to extend the distal portion of the RF electrode out of the distal portion of the cannula; and coupling the RF electrode to an RF generator.

In at least some aspects, the method further includes operating the actuator of the deployment mechanism to retract the distal portion of the RF electrode back into the distal portion of the cannula. In at least some aspects, the deployment mechanism is a slider deployment mechanism and the actuator is a slider, wherein operating the actuator of the deployment mechanism including sliding the slider of the sliding deployment mechanism to extend the distal portion of the RF electrode out of the distal portion of the cannula. In at least some aspects, the deployment mechanism is a rotational deployment mechanism and the actuator is a rotatable actuator, wherein operating the actuator of the deployment mechanism including rotating the rotatable actuator of the rotational deployment mechanism to extend the distal portion of the RF electrode out of the distal portion of the cannula.

In at least some aspects, the method further includes injecting a fluid into a fluid injection port of the integrated cannula/RF electrode and through the cannula. In at least some aspects, the integrated cannula/RF electrode further includes a fluid tube coupled to the cannula hub and the fluid injection port.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of radiofrequency (RF) ablation systems and methods of making and using the systems. The present disclosure is also directed to RF ablation systems and methods that include an integrated cannula and electrode, as well as methods of making and using the same.

Figure 1:
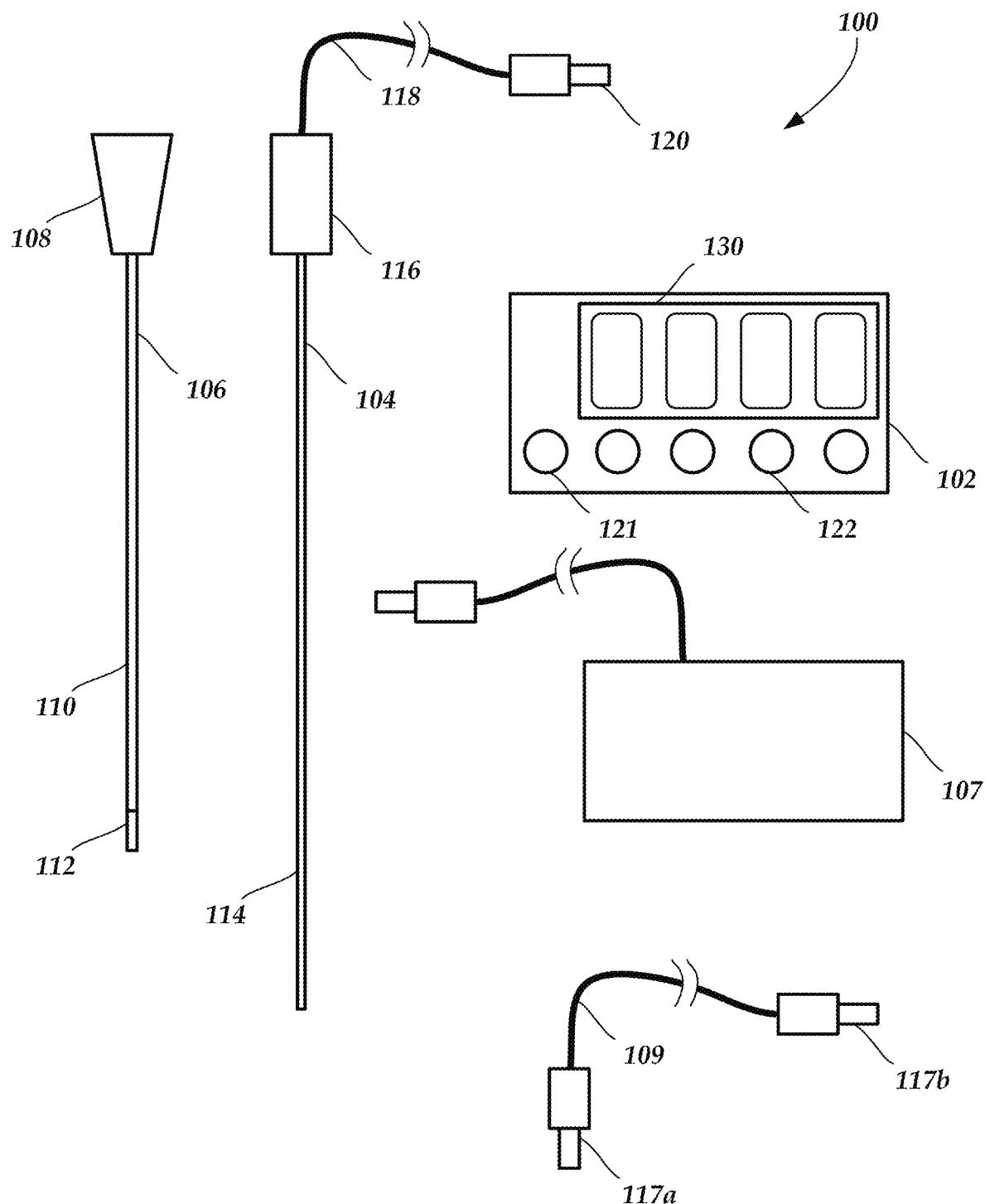
FIG. 1 is a schematic side view of components of one embodiment of an RF ablation system.

FIG. 1 illustrates one embodiment of an RF ablation system 100 that includes an RF generator 102, an RF electrode 104, a cannula 106, a ground pad 107, and an optional extension cable 109. The cannula 106 includes a cannula hub 108, an insulated shaft 110, and an active tip 112. The insulated shaft 110 is hollow with a cannula lumen for receiving the RF electrode 104. When inserted, the RF electrode 104 contacts, and energizes, the active tip 112 of the cannula 106 to produce RF ablation or electrical stimulation. The RF electrode 104 includes an electrode shaft 114, an electrode hub 116, a cable 118 that is electrically coupled to the electrode shaft 114, and a connector 120 for connecting to a port 122 of the RF generator 102 to energize the electrode shaft 114 via the cable 118 and connector 120. The optional adapter or extension 109 includes a cable 119 and connectors 117a, 117b for coupling the RF electrode 104 to the RF generator 102. It will be recognized that other RF ablation systems utilize the RF electrode 104 for ablation instead of, or in addition to, the cannula 106.

The RF generator 102 can include one or more ports 122 and at least one screen 130. In at least some embodiments, each port 122 is associated with a portion of the screen 130 (or a different screen) and can receive the connector 120 from an RF electrode 104. Information such as current, voltage, status, or the like or any combination thereof can be displayed on the screen 130. In at least some embodiments, each port 122 corresponds to an independent channel for operating an RF electrode 104. The RF generator 102 also includes a ground port 121 for attachment of the ground pad 107.

Examples of RF generators and RF ablation systems and methods of making and using the RF generators and RF ablation systems can be found at, for example, U.S. Pat. Nos. 9,717,552; 9,956,032; 10,111,703; 10,136,937; 10,136,942; 10,136,943; 10,194,971; 10,342,606; 10,363,063; 10,588,687; 10,631,915; 10,639,098; and 10,639,101 and U.S. Patent Application Publications Nos. 2014/0066917; 2014/081260; and 2014/0121658, all of which are incorporated herein by reference in their entireties.

Figure 2:
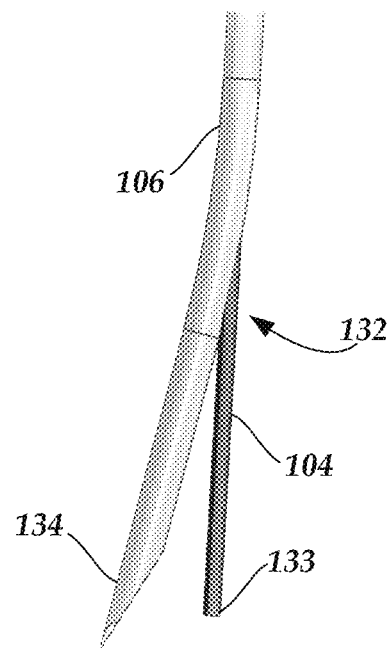
FIG. 2 is a schematic perspective view of distal ends of one embodiment of a cannula and RF electrode of an RF ablation system.

FIG. 2 illustrates an arrangement of the cannula 106 and RF electrode 104 in which the RF electrode extends out of an opening 132 of the cannula. In this arrangement, the RF electrode 104 contacts the cannula 106 so that the RF electrode can energize the cannula when the RF electrode is energized by the RF generator 104. The tip 133 of the RF electrode 104 also extends away from the tip 134 of the cannula 106 which may provide for a larger ablation or active area. In at least some instances, this arrangement of cannula 106 and RF electrode 104 is described as a "sidekick" arrangement. In this arrangement, the tip 133 of the RF electrode 104 is spaced apart from the tip 134 of the cannula 106 when the RF electrode is deployed out of the opening 132 of the cannula. In at least some embodiments, the tip 134 of the cannula 106 is occluded which then directs the tip 133 of the RF electrode 104 away from the cannula.

In some embodiments, the cannula 106 is bent and the RF electrode 104 is straight, as illustrated in FIG. 2, or bent in a different direction. In other embodiments, the cannula 106 is straight and the RF electrode 104 is bent. For example, the RF electrode 104 (or a distal portion of the RF electrode) can be bent and biased to exit out the opening 132 of the cannula.

During the RF ablation procedure, after the cannula 106 is placed into the patient, several components are inserted and removed from the cannula. For example, fluid can be injected through the cannula 106 to the target site and, in at least some instances, a fluid delivery tube is inserted into the cannula 106. As described above, the RF electrode 104 is also inserted into the cannula 106 after removal of a fluid delivery tube or any other component that has been inserted into the cannula. This movement can cause the cannula 106 to shift away from the target site, reducing the effectiveness of the ablation. Additionally, the insertion and removal of multiple components increases the time of the procedure.

As described herein, an integrated cannula/RF electrode can include an RF electrode (which may take the form of a tine or any other suitable structure) disposed within the shaft of the cannula during insertion into the patient and then the tip of the RF electrode can be deployed out of the cannula after placement. The integrated cannula/RF electrode includes a deployment mechanism to deploy and optionally retract the RF electrode relative to the cannula. In at least some embodiments, the deployment mechanism and the cable of the RF electrode extend from the cannula hub. Optionally, an injection tube can also extend from the cannula hub.

Figure 3:
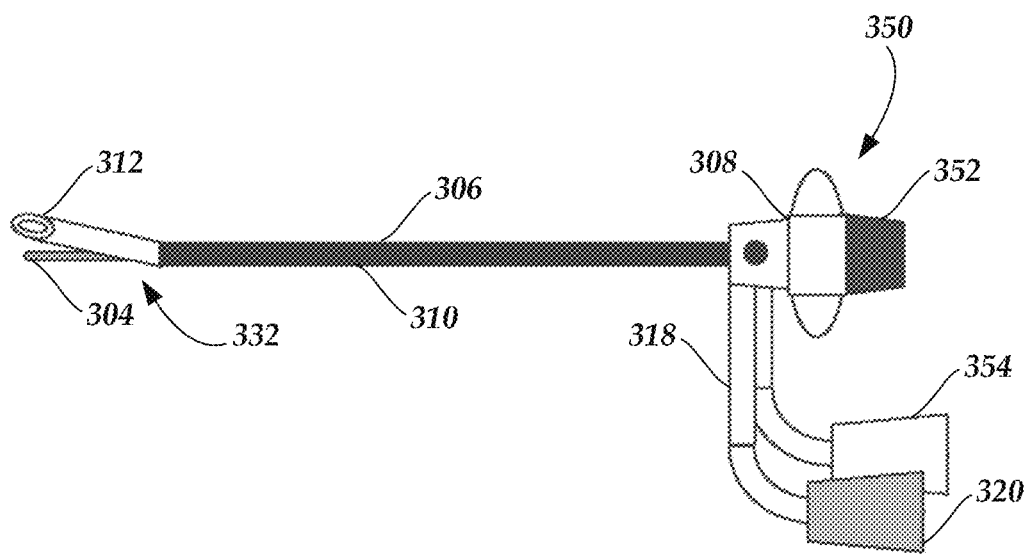
FIG. 3 is a schematic side view of one embodiment of an integrated cannula/RF electrode.

FIG. 3 illustrates one embodiment of an integrated cannula/RF electrode 350 with a cannula 306, an RF electrode 304 at least partially disposed within the cannula, a cannula hub 308, a deployment mechanism 352 attached or otherwise coupled to the cannula hub, a cable 318 extending from the cannula hub for coupling to the RF generator 102 (or an extension 109) using a connector 320, and an optional fluid injection tube 354 extending from (or fluid injection port disposed in or extending from) the cannula hub and arranged so that fluid can be injected into the injection tube (or injection port) and pass into the cannula hub and then along the cannula to the opening 332 in the cannula. In at least some embodiments, at least a portion of the RF electrode 304 of the integrated cannula/RF electrode 350 is permanently disposed in the cannula 306. The term "permanently" refers to the disposition of the RF electrode 304 in the cannula 306 after manufacture of the integrated cannula/RF electrode 350 and is intended to refer to normal storage and operation of the integrated cannula/RF electrode. It will be understood that, outside of normal storage and operation, the integrated cannula/RF electrode may be disassembled which will often preclude reassembly and use.

In at least some embodiments, the cannula 306 includes a shaft 310 and an active tip 312. In at least some embodiments, the shaft 310 is made of an insulating material or is insulated along the interior of the shaft. The active tip 312 is made of a conductive material such as metal (for example, titanium or any other suitable metal or alloy.) In at least some embodiments, the shaft 310 is made of conductive material which may be the same conductive material as the active tip. In at least some embodiments, the shaft 310 is insulated on an exterior of the shaft. In at least some embodiments, the shaft 310 is not insulated along the interior of the shaft.

Figure 4:
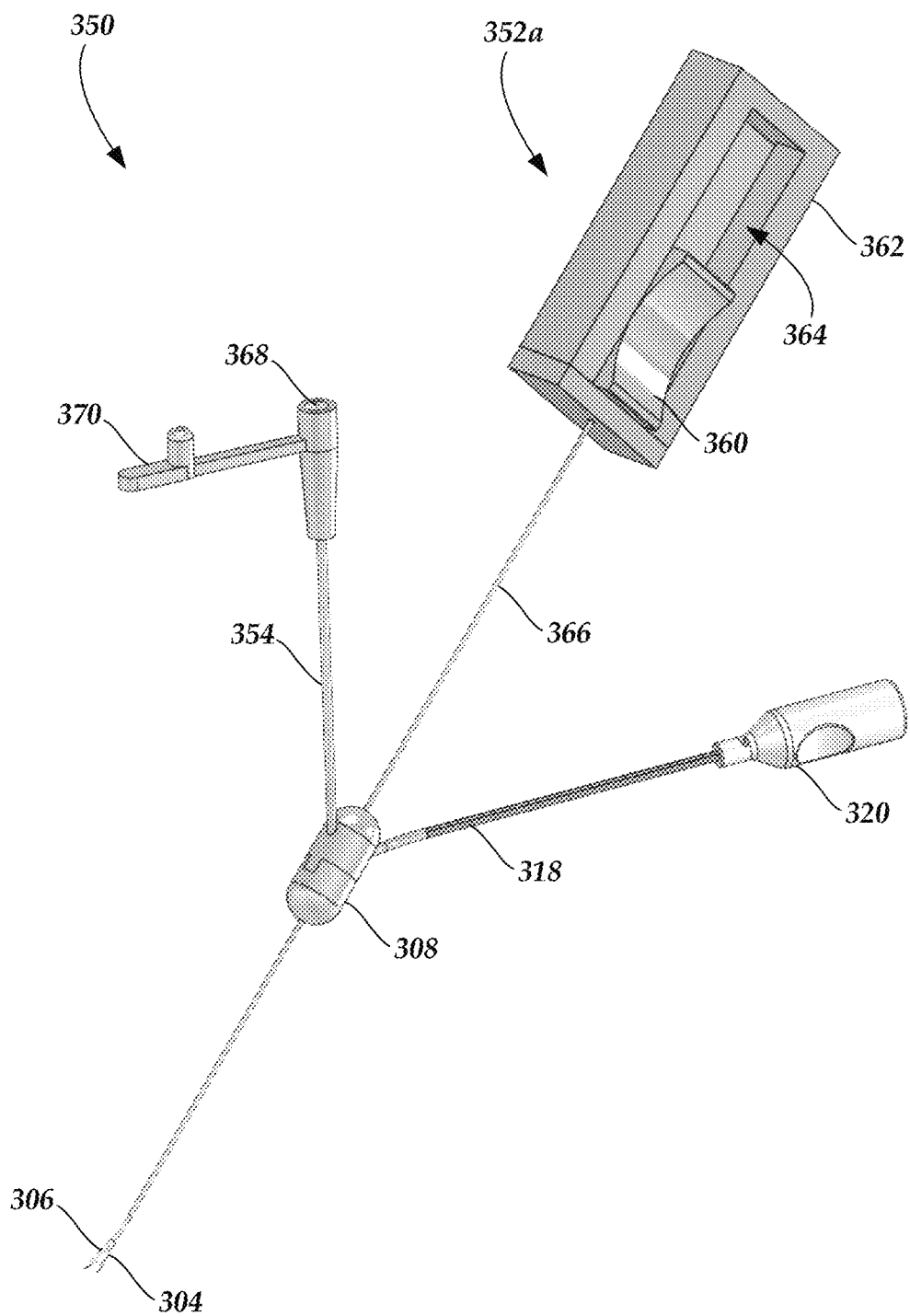
FIG. 4 is a schematic perspective view of another embodiment of an integrated cannula/RF electrode with a slider deployment mechanism.

FIG. 4 illustrates one embodiment of an integrated cannula/RF electrode 350 that utilizes a slider deployment mechanism 352a having an actuator that includes a slider 360, a case 362 defining a track 364 for the slider, and a rod 366 attached to the slider 360. The rod 366 extends into the cannula hub 308 and is coupled to the RF electrode 304 or may even be part of the RF electrode. The slider 360, case 362, and rod 366 can be made of any suitable material including, but not limited to, metal, rigid or stiff plastic, or the like or any combination thereof. In at least some embodiments, the rod 366 is an electrical insulator or is electrically insulated from the RF electrode 304. In at least some embodiments, the rod 366 is a wire that is sufficiently stiff to push the RF electrode 304 out of the cannula and retract the RF electrode back into the cannula.

In some embodiments, the slider deployment mechanism 352a can be attached directly to the cannula hub 308 instead of spaced apart from the cannula hub, as illustrated in FIG. 4.

The integrated cannula/RF electrode 350 of FIG. 4 also includes a cable 318 extending from the cannula hub 308 and having a connector 320 at the other end of the cable for coupling to an RF generator 102 or an extension 109. The cable 318 includes wires that electrically couple (for example, by laser welding or any other suitable attachment technique) to the RF electrode 304.

In operation, after the cannula 306 has been inserted into the patient, the slider 360 can be pushed to drive the tip or distal portion of the RF electrode 304 out of the cannula 306. The connector 320 is coupled to the RF generator 102 (FIG. 1), or to an extension 109 (FIG. 1) that is coupled to the RF generator. The RF generator 102 then energizes the RF electrode 304 and cannula 306 for ablation, stimulation, or the like. In at least some embodiments, when treatment is completed, the slider 360 can be retracted to retract the tip of the RF electrode 304 back into the cannula 306.

The integrated cannula/RF electrode 350 of FIG. 4 also includes a fluid injection tube 354 with a port 368 and optional attached cap 370 for sealing the port. The fluid injection tube 354 extends into the cannula hub 308 and permits fluid to be injected into the cannula 306 and out the opening 332 (FIG. 3) in the cannula. In at least some embodiments, fluid injection can occur even when the tip or distal portion of the RF electrode 304 is retracted into the cannula 306. In other embodiments, a port 368 can be formed in the cannula hub 308 for fluid injection directly into the cannula hub. In at least some embodiments, the cannula hub 308 includes a seal (not shown) around the entry point of the rod 368 into the cannula hub to prevent injected fluid from exiting through that opening in the cannula hub.

Figure 5:
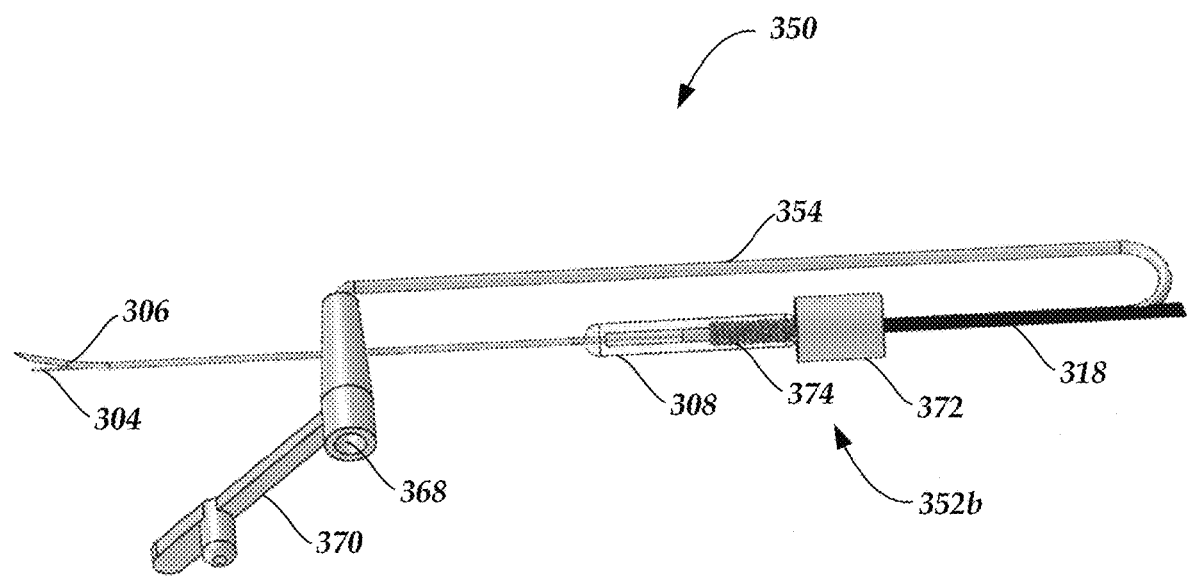
FIG. 5 is a schematic perspective view of a third embodiment of an integrated cannula/RF electrode with a rotational deployment mechanism.
Figure 6:
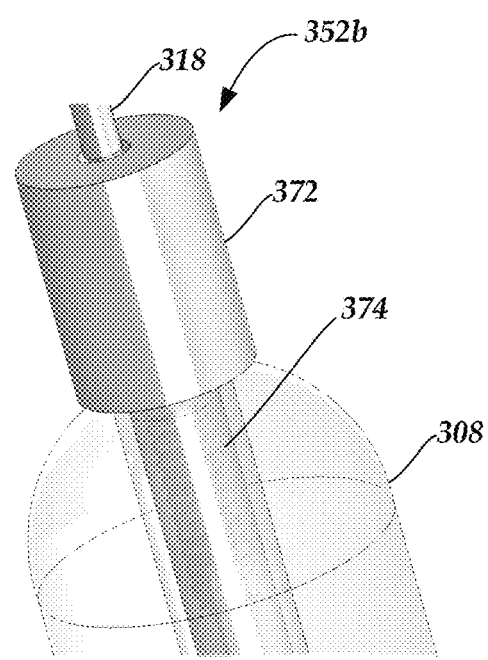
FIG. 6 is a schematic perspective view of a portion of the rotational deployment mechanism of FIG. 5.

FIG. 5 illustrates one embodiment of an integrated cannula/RF electrode 350 that utilizes a rotational deployment mechanism 352b that includes an actuator in the form of a rotatable actuator 372 and a screw 374 that is rotated by the rotatable actuator to extend or retract the screw. FIG. 6 is a close-up of the rotatable actuator 372 and portions of the screw 374 and cannula hub 308. In at least some embodiments, the rotatable actuator 372 includes an interior lumen (not shown) that is threaded and receives the threads of the screw 374. In at least some embodiments, the cannula hub 308 also includes a tapped hole with threads to receive the threads of the screw 374. The screw 374 is disposed in the cannula hub 308 and is coupled to the RF electrode 304 or may even be part of the RF electrode. The screw 374 and rotatable actuator 372 can be made of any suitable material including, but not limited to, metal, rigid or stiff plastic, or the like or any combination thereof. In at least some embodiments, the screw 374 or rotatable actuator 372 is an electrical insulator or is electrically insulated from the RF electrode 304.

In some embodiments, the rotational deployment mechanism 352b can be spaced apart from the cannula hub 308 instead of part of (or directly attached to) the cannula hub, as illustrated in FIG. 5.

The integrated cannula/RF electrode 350 of FIG. 5 also includes a cable 318 extending from the cannula hub 308 and having a connector 320 (FIG. 3) at the other end of the cable for coupling to an RF generator 102 or an extension 109. The cable 318 includes wires that electrically couple (for example, by laser welding or any other suitable attachment technique) to the RF electrode 304. In the illustrated embodiment of FIG. 5, the cable extends into the rotatable actuator 372 and is electrically coupled to either the screw 374 or the RF electrode 304. In at least some embodiments, the cable 318 is coupled.

In operation, after the cannula has been inserted into the patient, the rotatable actuator 372 can be rotated in one direction to extend the screw 374 and drive the tip or distal portion of the RF electrode 304 out of the cannula 306. The connector 320 is coupled to the RF generator 102 (FIG. 1), or to an extension 109 (FIG. 1) that is coupled to the RF generator. The RF generator 102 then energizes the RF electrode 304 and cannula 306 for ablation, stimulation, or the like. In at least some embodiments, when treatment is completed, the rotatable actuator 372 can be rotated in the opposite direction to retract the screw 374 and retract the tip of the RF electrode 304 back into the cannula 306.

The integrated cannula/RF electrode 350 of FIG. 5 also includes a fluid injection tube 354 with a port 368 and optional attached cap 370 for sealing the port. The fluid injection tube 354 extends into the cannula hub 308 and permits fluid to be injected into the cannula 306 and out the opening 332 (FIG. 3) in the cannula. In at least some embodiments, fluid injection can occur even when the tip or distal portion of the RF electrode 304 is retracted into the cannula 306. In other embodiments, a port 368 can be formed in the cannula hub 308 for fluid injection directly into the cannula hub. In at least some embodiments, the cannula hub 308 includes a seal (not shown) around the coupling of the rotatable actuator 372 to the cannula hub, or the entry point of the screw 374 into the cannula hub, to prevent injected fluid from exiting through that opening in the cannula hub.

In at least some embodiments, the cable 318 (and its wires) are coupled to the fluid injection tube 354 using epoxy or other adhesive. The RF electrode is electrically coupled to the wires of the cable 318. This arrangement is inserted through a hollow screw 374 which is inserted into the cannula hub.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. An integrated cannula/RF electrode for an RF ablation system, the integrated cannula/RF electrode comprising:
    a cannula comprising a cannula hub and a shaft extending from the cannula hub, wherein the shaft comprises a distal portion;
    an RF electrode comprising a distal portion, wherein at least a portion of the RF electrode is permanently disposed within the cannula; and
    a deployment mechanism coupled to the RF electrode and either coupled to the cannula hub or extending from the cannula hub, wherein the deployment mechanism comprises an actuator coupled to the RF electrode and is configured to extend the distal portion of the RF electrode out of the distal portion of the shaft of the cannula by actuation of the actuator, wherein the integrated cannula/RF electrode is configured so that the RF electrode, when extended, is in electrical contact with the distal portion of the cannula so that, when the RF electrode is energized, the distal portion of the cannula is also energized, wherein the deployment mechanism further comprises an insulated rod having a proximal portion and a distal portion, wherein the actuator is coupled to the proximal portion of the insulated rod and the RF electrode is coupled to the distal portion of the insulated rod.

2. The integrated cannula/RF electrode of claim 1, wherein the deployment mechanism is further configured to retract the distal portion of the RF electrode back into the cannula.

3. The integrated cannula/RF electrode of claim 1, further comprising a cable extending from the cannula hub and electrically coupled to the RF electrode.

4. The integrated cannula/RF electrode of claim 1, wherein a portion of the interior of the shaft is electrically insulated.

5. The integrated cannula/RF electrode of claim 1, wherein the distal portion of the shaft of the cannula is bent and the RF electrode is straight.

6. The integrated cannula/RF electrode of claim 1, wherein the deployment mechanism is a slider deployment mechanism and the actuator is a slider.

7. The integrated cannula/RF electrode of claim 6, wherein the slider deployment mechanism further comprises a case that defines a track for the slider.

8. The integrated cannula/RF electrode of claim 1, wherein the deployment mechanism is a rotational deployment mechanism and the actuator is a rotatable actuator.

9. The integrated cannula/RF electrode of claim 8, wherein the rotational deployment mechanism further comprises a screw coupled to the rotatable actuator and the RF electrode.

10. The integrated cannula/RF electrode of claim 9, wherein the screw is hollow.

11. The integrated cannula/RF electrode of claim 1, further comprising a fluid injection port for injecting fluid through the cannula hub and the cannula.

12. The integrated cannula/RF electrode of claim 11, further comprising a fluid tube coupled to the cannula hub and the fluid injection port.

13. An RF ablation system, comprising:
    the integrated cannula/RF electrode of claim 1; and
    an RF generator coupleable or coupled to the integrated cannula/RF electrode.

14. The RF ablation system of claim 13, further comprising an extension configured to couple the integrated cannula/RF electrode to the RF generator.

15. A method of using the integrated cannula/RF electrode of claim 1, the method comprising:
    operating the actuator of the deployment mechanism to extend the distal portion of the RF electrode out of the distal portion of the cannula; and
    coupling the RF electrode to an RF generator.

16. The method of claim 15, further comprising operating the actuator of the deployment mechanism to retract the distal portion of the RF electrode back into the distal portion of the cannula.

17. The method of claim 15, further comprising injecting a fluid into a fluid injection port the integrated cannula/RF electrode and through the cannula.

* * * * *